United States Patent
Keller et al.

(10) Patent No.: US 10,413,348 B2
(45) Date of Patent: Sep. 17, 2019

(54) ARRANGEMENT FOR CONTACT COAGULATION OF BIOLOGICAL TISSUE

(71) Applicant: ERBE ELEKTROMEDIZIN GMBH, Tuebingen (DE)

(72) Inventors: Sandra Keller, Hechingen (DE); Marc Kegreiss, Tuebingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 550 days.

(21) Appl. No.: 14/838,451

(22) Filed: Aug. 28, 2015

(65) Prior Publication Data
US 2016/0066978 A1 Mar. 10, 2016

(30) Foreign Application Priority Data
Sep. 5, 2014 (EP) .................................. 14183771

(51) Int. Cl.
*A61B 18/12* (2006.01)
*A61B 18/14* (2006.01)
*A61B 18/00* (2006.01)

(52) U.S. Cl.
CPC .......... *A61B 18/1233* (2013.01); *A61B 18/14* (2013.01); *A61B 2018/00589* (2013.01);
(Continued)

(58) Field of Classification Search
CPC ................ A61B 18/1233; A61B 18/14; A61B 2018/00589; A61B 2018/00642;
(Continued)

(56) References Cited

U.S. PATENT DOCUMENTS

| 2002/0165530 A1 | 11/2002 | Harano et al. |
| 2002/0165531 A1 | 11/2002 | Goble |

(Continued)

FOREIGN PATENT DOCUMENTS

| CN | 100484493 C | 5/2009 |
| CN | 102764152 A | 11/2012 |

(Continued)

*Primary Examiner* — Michael F Peffley
*Assistant Examiner* — Tigist S Demie
(74) *Attorney, Agent, or Firm* — Blank Rome LLP

(57) ABSTRACT

An arrangement having a device for providing high-frequency voltage $U_{App}$ for contact coagulation of the biological tissue. The device is equipped to operate with a high voltage that is normally not suitable for contact coagulation, but otherwise used for spark coagulation, for example, more than 400V at the beginning of the contact coagulation. During the operation of the generator the tissue impedance $\underline{Z}$ is monitored. This can occur by means of continuously measuring the voltage $U_{App}$ of the flowing current $I_{App}$ and the phasing $\varphi$ between the voltage and the flowing current. Using both, the measuring unit continuously determines the tissue impedance $\underline{Z}$. A minimum detector is provided to determine if an impedance minimum $\underline{Z}_{min}$ has passed through and if such is found, to induce the generator control to reduce the voltage $U_{App}$ delivered by the device to a value that avoids spark generation as well as desiccation of the tissue.

14 Claims, 3 Drawing Sheets

(52) U.S. Cl.
CPC .............. *A61B 2018/00642* (2013.01); *A61B 2018/00672* (2013.01); *A61B 2018/00678* (2013.01); *A61B 2018/00767* (2013.01); *A61B 2018/00827* (2013.01); *A61B 2018/00869* (2013.01); *A61B 2018/00875* (2013.01); *A61B 2018/00988* (2013.01)

(58) Field of Classification Search
CPC ........... A61B 2018/00672; A61B 2018/00678; A61B 2018/00767; A61B 2018/00827; A61B 2018/00869; A61B 2018/00875; A61B 2018/00988
See application file for complete search history.

(56) References Cited

U.S. PATENT DOCUMENTS

2003/0158551 A1* 8/2003 Paton ................. A61B 18/1206
606/51
2012/0283730 A1 11/2012 Schell

FOREIGN PATENT DOCUMENTS

| | | |
|---|---|---|
| DE | 36 22 337 A1 | 1/1988 |
| EP | 1 862 137 A1 | 12/2007 |
| EP | 2 520 240 A1 | 11/2012 |
| JP | 2002-325772 A | 11/2002 |
| JP | 2012-232141 A | 11/2012 |
| RU | 2 294 171 C2 | 2/2007 |

* cited by examiner

ARRANGEMENT FOR CONTACT COAGULATION OF BIOLOGICAL TISSUE

TECHNICAL FIELD

Embodiments of the invention relate to an arrangement for contact coagulation of biological tissue upon exposure to electrical current.

BACKGROUND

In contact coagulation of biological tissue, primarily thermally induced processes take place that lead to, among other things, to the denaturing of the tissue whereby any hollow vessels that are present are intended to be closed. When applying a high-frequency voltage to biological tissue a very high electric impedance of the tissue can be observed at the beginning of the process. The current of electrical charge carriers passes primarily through extracellular fluids as a result of which the tissue starts to heat up due to the kinetic energy of the displaced carriers of the electric charge. As the tissue is increasingly heated, the impedance decreases until it reaches a minimum. The increase of the electric conductivity occurs in a temperature range of 60° C. to 100° C. of the biological tissue due to its temperature-induced structural changes that accompany the denaturing of the tissue. The tissue is devitalized; the protein molecule clump together, the cell membrane is destroyed as a result of which tissue fluid is released. In this "phase I", the tissue impedance $Z$ continually decreases. After some time, the boiling temperature of the tissue fluid is reached, whereby the tissue resistance once again increases, which is described as "phase II". Generally, the tissue impedance $Z$ reaches values in phase II that are clearly above the impedance minimum of the tissue and often the initial impedance in phase I.

EP 2 520 240 A1 discloses a method and an arrangement for tissue fusion and also for coagulation in which by specifying a negative internal resistance of a supplying high-frequency source, a constantly consistent treatment time is intended to be achieved.

EP 1 862 137 A1 discloses a device and a method for coagulation of tissue in which the tissue impedance $Z$ is polled and monitored. By means of continual readjustment of the electrical energy delivered to the tissue it is achieved that the impedance of the tissue follows a desired, specified curve. In particular, this applies to phase II.

Further, DE 36 22 337 A1 discloses a high-frequency generator with automatic power control for a high-frequency coagulation that has an electric arc display device to detect an arc between the coagulation sensor and the tissue. In order to securely spark the electric arc, initially, the maximum amount of output power is used. After the electric arc is sparked, at first maximum power continues to be supplied for a certain period of time. The output power is then reduced to zero for a predetermined second interval. As long as the generator is activated, these cycles continue to be repeated.

By means of the method described by DE 36 22 337 A1, a coagulation mode is achieved in which the coagulation initially starts with contact coagulation, whereby after reaching the boiling temperature of the tissue fluid, an electric arc penetrates the vapor that is forming, whereby the current density is highly elevated at the penetration site of the electric arc, as a result of which a marked local coagulation effect occurs and the tissue takes on high impedance. The electric arc sparks and jumps to various locations until the entire tissue in the proximity of the coagulation sensor has high impedance, i.e. has coagulated. Switching off of the electric arc intermittently by setting the output line to zero prevents excessive burning, i.e. an overly strong carbonization of the tissue.

In the case of a fast coagulation that is based on the formation of sparks or which permits such, the tissue can adhere to the instrument and thus lead to an accompanying significant contamination of the instrument and also the treatment personnel. Moreover, the carbonization can impede the wound-healing process.

If a fast coagulation without an electric arc is brought about by pure contact coagulation in phase I with elevated high-frequency power delivered by a high-frequency generator, an acutely audible and visually perceivable tearing of the treated tissue can occur. This is caused by local tearing of tissue due to boiling tissue fluid and the accompanying increase in tissue pressure. Due to the tearing of the tissue, previously stopped bleeding can start to bleed anew. Furthermore, treated pathogenic tissue can disseminate into healthy tissue areas due to the tearing and also be absorbed by the attending personnel.

SUMMARY

It is the objective of embodiments of the invention to propose a concept by means of which tissue coagulation can be achieved quickly while applying gentle treatment.

The arrangement for contact coagulation of biological tissue according to an embodiment of the invention has a generator for providing high-frequency voltage and for delivering high-frequency current. A generator control is provided that is in a position to influence the high-frequency voltage provided. Furthermore, the arrangement includes an instrument having at least one electrode that is supplied by the generator with high-frequency current. A measuring unit monitors the tissue impedance.

A minimum detector is provided for detecting a minimum of the tissue impedance. If a minimum of the tissue impedance is detected, the generator is induced to provide a reduced high-frequency voltage.

It has been shown that the tearing of tissue that is partially or entirely coagulated already is accompanied by crossing the minimum of the tissue impedance $Z$. The tissue has reached its most conductive condition at the impedance minimum. This occurs prior to reaching the boiling point of the tissue fluid already, i.e. before a temperature of 100° C. has been reached. After that, when high-frequency voltage is applied, the tissue fluid will vaporize. Such a vaporization leads to an increase in pressure in the tissue and to its tearing, which is avoided by embodiments of the invention. Thereby, it is also avoided that contaminated tissue scatters, that open wounds and instruments are contaminated and OP personnel is soiled or infected. Furthermore, tearing of blood vessels that have already coagulated, lymphatic vessels or other vessels is avoided. Due to the continuation of the coagulation at a reduced voltage, the coagulation can be continued without such effects until the desired tissue effect develops.

The proposed new contact coagulation mode works with elevated power input until the impedance minimum is reached. Hereby, in phase I, up to reaching the impedance minimum, the maximum possible high-frequency energy is supplied by feeding an elevated high-frequency voltage into the tissue. The start of the coagulation occurs upon contact of the instrument with the tissue at the maximum power output of the generator, i.e. with a high-frequency voltage that is preferably significantly above 200V, independent of the current. The generation of vapor in the tissue and thus the tearing of tissue is prevented, however, by interrupting the application of elevated high-frequency voltage as soon as an impedance minimum is detected. Subsequently, only a reduced high-frequency voltage is applied.

In a preferred embodiment, an adjustment value for the voltage to be applied is stored in the generator control. The generator control is then equipped to induce the generator— at the start of a coagulation program—to provide the voltage that is to be applied at a value that is higher than the adjustment value. Preferably, the voltage to be applied at the beginning of the coagulation process is at least twice as high as the adjustment value. When the user sets the customary voltage suitable for contact coagulation (e.g. 200V), the user works with a voltage of at least 400V at the start of the coagulation process in the system according to embodiments of the invention. However, this does not cause any spark formation because the voltage is reduced as soon as an impedance minimum has been passed and there is a risk of vapor formation. By avoiding vapor formation, the generation of sparks and the accompanying bursting of vapor bubbles in the tissue and its concomitant disadvantages can be avoided.

In a preferred embodiment, after detecting the first minimum of tissue impedance, the generator is induced to provide the voltage that is to be applied at a value that is no higher than the adjustment value. Thereby, the adjustment value is preferably specified at a value that makes continuous coagulation possible without any spark formation. Preferably, the generator control is equipped to respond to the detection of a second or further minimum of the tissue impedance $\underline{Z}$ by inducing the generator to reduce the voltage to be applied to a value that is lower than the adjustment value. Preferably, this value is lower by a specified percentage, for example, 10% lower than the previously delivered voltage.

Further, the generator control can be equipped to terminate the high-frequency application of the generator when the voltage to be applied has reached a value that does not exceed or is below a specified fraction of the adjustment value. This specified fraction can, for example, amount to 60% of the set voltage. With such an arrangement, a quick and large-volume coagulation is achieved. The adjustment value of the voltage to be applied can be specified in steps or continuous. Preferably, corresponding adjustment means are provided at the device supplying the instrument. The monitoring of the tissue impedance can be continuous or at closely successive points in time, as it were continuous. Preferably, the time intervals between individual measurements of the tissue resistance are smaller than 0.2 msec. Preferably, the time intervals are approx. 100 μsec. Thereby, the changing tissue resistance can be met with a fast response.

When capturing the actual tissue impedance at short time intervals, preferably, the provided, applied voltage and the current flowing through the biological tissue as well as their phasing relative to each other are captured in time windows that have a length that is at least as long as one oscillation period, further, advantageously at least as long as several oscillation periods of the high-frequency voltage. Thereby, preferably at least one parameter of the voltage applied and at least one parameter of the flowing current are captured. A parameter of the voltage can be the peak-peak voltage (double the peak voltage), the peak voltage (single peak voltage), the average value of the voltage, the rectified value, the rms-value or the like. This correspondingly applies to the flowing current. The peak-to-peak current (double the peak current), the peak current (simple peak current) the average value of the amount of current, the rectified value, the rms-value or the like can be a parameter of the current. A parameter for the phasing can be the phase angle φ between the two cited parameters that describes the offset of the two parameters with respect to each other.

The tissue impedance $\underline{Z}$ can be the ratio of a parameter of the voltage and a parameter of the current relative to the phasing. In an advantageous embodiment, this ratio is compared with one or more previously determined ratios in order to detect reaching or crossing a tissue resistance minimum. The minimum detector is equipped to signal the tissue impedance minimum to the generator control.

$$\underline{Z} = \frac{u(t)}{i(t)} = Z \cdot e^{j\psi} = Z(\cos\psi + j \cdot \sin\psi) = R + jX;$$

$$|\underline{Z}| = Z, \ Z = \frac{Up}{Ip} = \frac{Urms}{Irms}$$

In a different embodiment, the minimum detector can be equipped to determine the trend of the tissue impedance with the help of measured tissue impedances in order to make a prognosis for the next tissue impedance to be measured, whereby reaching and crossing a tissue impedance minimum is signalized then, when the next measured tissue impedance $\underline{Z}$ is above a predetermined value of the prognosis for the next tissue impedance to be measured. Thereby, the reaching of the tissue impedance minimum can be captured prior to its resurgence and the formation of vapor bubbles is suppressed even faster.

Further details of embodiments of the invention are the subject matter of the drawing, the description, or claims.

DETAILED DESCRIPTION

Figure 1:
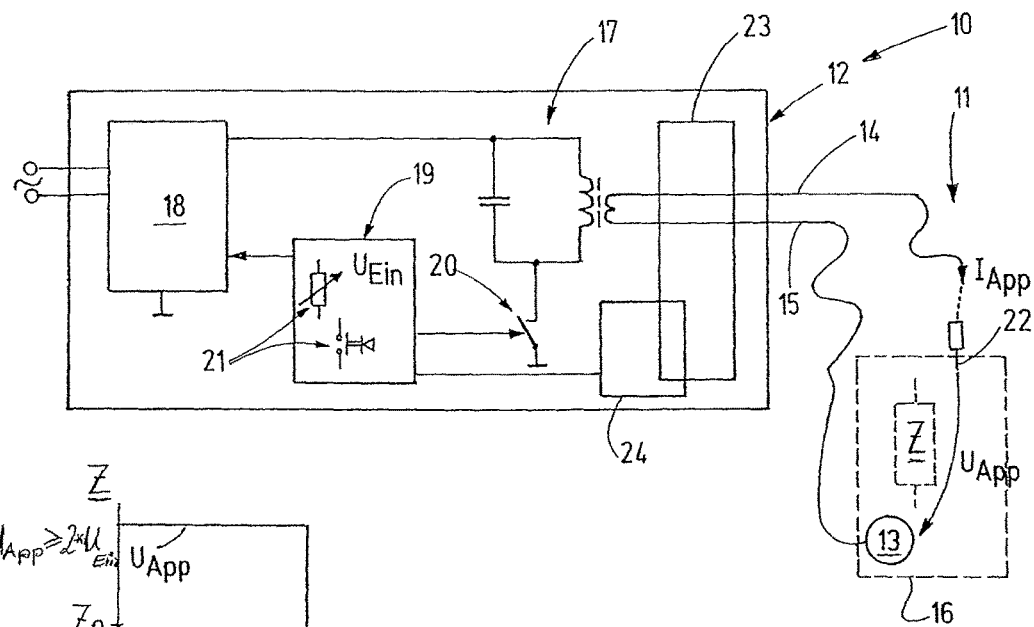
FIG. 1 shows the arrangement according to an embodiment of the invention with a generator and an instrument in schematic illustration.

FIG. 1 illustrates an arrangement 10 for contact coagulation of biological tissue that includes an instrument 11 and a supplying device 12. Instrument 11 and a neutral electrode 13 that serves as a return system are respectively connected to device 12 by cable 14, 15. Biological tissue 16 that is to be coagulated in sections by means of instrument 11 and which closes the electric circuit between instrument 11 and neutral electrode 13 is shown symbolically in FIG. 1 by a dotted block. The biological tissue 16 has a tissue impedance $\underline{Z}$ that has an ohmic component R and can have more or less large reactive components jX, in particular, a capacitive component.

$$R=Z^*\cos\varphi, X=Z^*\sin\varphi$$

Device 12 contains a generator 17 for generating high-frequency electric voltages and currents. Generator 17 is connected to an operating voltage that is provided by a power supply unit 18. The operation of generator 17 is determined by a generator control 19 that controls, for example, an electronic switching element or repeater 20 in order to excite an oscillating circuit belonging to generator 17. Generator control 19 can have one or several operating elements 21 aufweisen, by means of which the user can make specifications for the operation of the generator and settings. For example, the settings to be initialized can include an adjustment value $U_{Ein}$ by means of which the user sets voltage values familiar to him for the contact coagulation, (for example, 200V). Further, the adjustment values can include the type of operation or other parameters, for example, the desired coagulation volume or the desired coagulation time, the energy that is to be applied at a maximum or the like. Furthermore, other parameters such as the crest factor, maximum current, maximum power and the like can be adjustable. Generator 17 provides a voltage $U_{App}$ that is available at electrode 22 of instrument 11 and based on which a current $I_{App}$ flows through tissue 16. The voltage $U_{App}$ applied to the tissue and the current $I_{App}$ flowing through the tissue are captured by a measuring unit 23 and measured values are derived from such. Measuring unit 23 uses the measured value of current $I_{App}$ and the measured value of voltage $U_{App}$ and determines the actual tissue impedance $\underline{Z}$. Thereby, a minimum detector 24 is provided in order to detect whether or when the tissue impedance $\underline{Z}$ has been reached or passed through. In such a case, the minimum detector 24 signals this to generator control 19.

Figure 3:
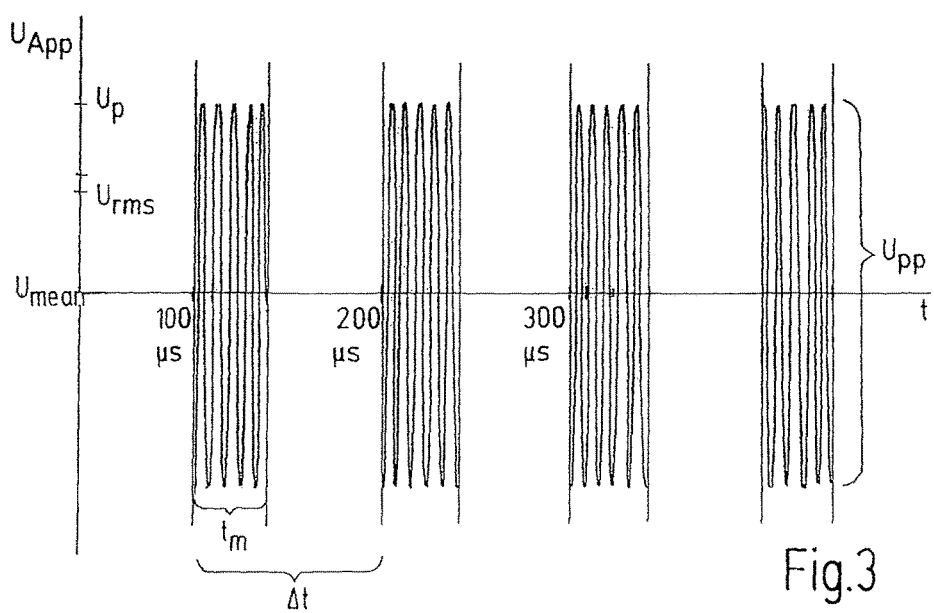
FIG. 3 is a time diagram illustrating the measurement of the tissue resistance.

The generator control 19, the measuring unit 23 and the minimum detector 24 are functional blocks. Structurally, they can be integrated into a single module or be subdivided into several individual modules. In particular, the measurement unit 23 and the minimum detector 24 can be combined with the generator control into one module. The modules can be physical modules or also program modules or the like. For example, measuring unit 23 can convert the current $I_{App}$ to be measured as well as also the voltage $U_{App}$ to be measured into data pairs by means of analogue/digital converters and then, by means of a computation block determine the pertaining tissue impedance values. The tissue impedance values can be held accessible in a memory for further processing, for example. The minimum detector 24 can be formed by a program routine that searches for an impedance minimum in the data pairs. Thereby, the tissue impedance can be defined as the ratio of one of the parameters of the respectively measured voltage $U_{App}$ and one of the parameters of the measured current $I_{App}$. FIG. 3 illustrates the measurement of the voltage $U_{App}$. For example, at short intervals $\Delta t$ of preferably less than 0.2 msec, preferably at time intervals $\Delta t$ of only 100 µsec, the voltage $U_{App}$ and the current $I_{App}$ (i.e. respectively at least one parameter) are measured. For this, FIG. 3 shows a respective time window $t_m$, that is slightly shorter than the time interval $\Delta t$. During time window $t_m$, at least one suitable voltage value, for example, the peak value $U_p$, the double peak value $U_{pp}$, the average value of the amount of voltage $U_{mean}$, the rms-value $U_{rms}$ or a similar parameter is measured for the voltage. Correspondingly, a parameter for the current is measured. This in turn can be the current peak value $I_p$, the average amount of current $I_{mean}$ or the rms-value $I_{rms}$. Further, a parameter is measured for the phasing. This can be the displacement angle $\varphi$ between the voltage and the current. Thus, for each measurement interval, the tissue impedance is given as the ratio of one of the measured parameters for the voltage $U_{App}$ (e.g. $U_p$, $U_{pp}$, $U_{mean}$ or $I_{rms}$) and a parameter of the current $I_{App}$ (e.g. $I_p$, $I_{pp}$, $I_{mean}$ or $I_{rms}$) relative to the phasing of the measured parameters for the voltage and the current.

Figure 2:
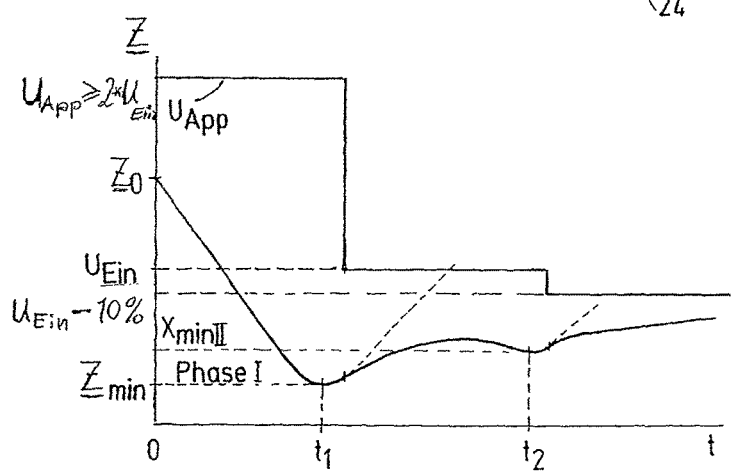
FIG. 2 is a graph showing the functioning of the generator of FIG. 1.

The generator control 19 is equipped to specify various generator voltages $U_{App}$ for the tissue impedance $\underline{Z}$ with the help of the measured or calculated values as is shown in general in FIG. 2. At the start of the contact coagulation, the not yet influenced biological tissue has an initial impedance of $\underline{Z}_0$. The generator 17 works with a voltage $U_{App}$ that is specified by the generator control corresponding to the adjustment value $U_{Ein}$. If the adjustment value $U_{Ein}$ is specified, for example, at a value of 200V for the contact coagulation that normally prevents spark generation, the generator control 19 now specifies a significantly higher value, preferably at least a value that is twice as high, for example, 400V or higher as application voltage $U_{App}$. Correspondingly, the generator 17 supplies a voltage $U_{App}$ von 400V or more. The resulting high current $I_{App}$ leads to a fast heating of the tissue 16, whereby a steep decline of tissue impedance $\underline{Z}$ occurs. If the minimum detector 24 detects that the minimum impedance $\underline{Z}_{min}$ has been passed at a point in time t1 or shortly thereafter, it sends a corresponding signal to generator control 19 so that it reduces the current $U_{App}$ that is applied to the tissue 16. Preferably, the voltage $U_{App}$ is reduced to the adjustment value $U_{Ein}$. As a result, the spark generation that would be possible after crossing the impedance minimum $\underline{Z}_{min}$ due to boiling processes being initiated and corresponding electrical flashovers and vapor bubbles, is prevented. Thus, a steeper rise of the tissue impedance as it could occur due to premature desiccation of tissue is also prevented. For example, if at point in time t2 a further impedance minimum $\underline{Z}_{minII}$ it will again be captured by minimum detector 24 and reported to the generator control 19 so that it once again reduces the voltage $U_{App}$ that is applied and thus reduces it further, for example, by 10%.

The process can be continued until the voltage $U_{App}$ that is applied reaches a lower limit value that can be, for example, 60% of the adjustment value $U_{Ein}$. If this is the case, the generator control can interrupt the activation by controlling the electronic switching element 20. Thereby, the coagulation is terminated.

Figure 4:
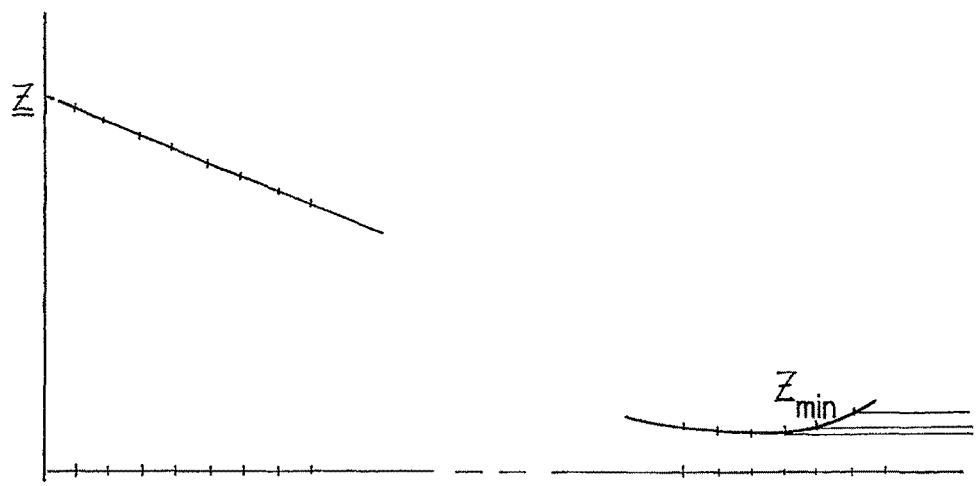
FIGS. 4 through 8 show additional diagrams to illustrate the operation of the arrangement in various embodiments.
Figure 5:
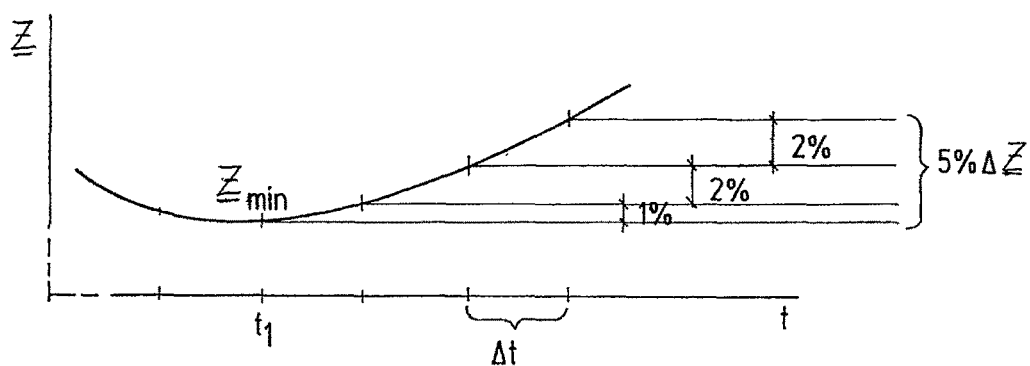

The minimum detector 24 can determine the impedance minimum according to each method that is suitable for an analysis of the data that was collected. FIGS. 4 and 5 thereby illustrate the relationships in the proximity of the impedance minimum. Thereby, for illustration, first an ideal signal sequence is assumed: After reaching an impedance minimum $\underline{Z}_{min}$ at a point in time t1 the tissue impedance $\underline{Z}$ rises again, whereby the percentage increases from one step to another can be relatively small. Furthermore, the measured values can be subject to an uncertainty of measurement, i.e. include noise, so that the small increases in impedance from one step to another are unsuitable for determining a minimum. This applies even more the smaller the time intervals $\Delta t$ between successive scans. In order to make the signal noise ineffective, such an increase in impedance is, for example, specified as criteria for the resurgence of the impedance that is not present in normal signal noise, i.e. that is higher than the signal noise. Such an increase in impedance can, for example, be a threshold of 5% that consequently does not occur in successive steps.

$$\frac{\Delta \underline{Z}}{\Delta t} = \frac{\underline{Z}_{m+1} - \underline{Z}_m}{t_{m+1} - t_m} \geq 5\%$$

Figure 6:
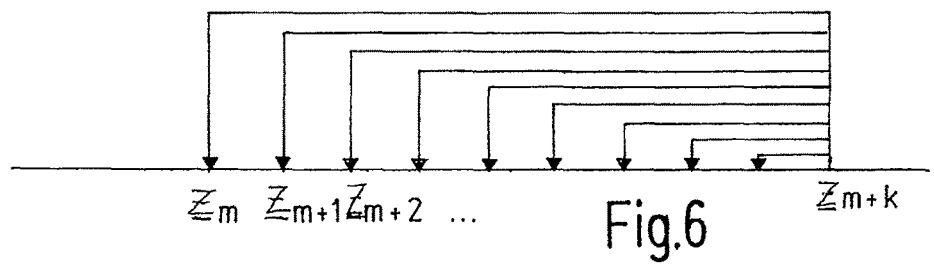

For detecting the increase in tissue impedance, the actually measured tissue impedance $\underline{Z}_{m+k}$ according to FIG. 6 can be compared with a series of preceding impedance measurement values $\underline{Z}_m$, $\underline{Z}_{m+1}$, $\underline{Z}_{m+2}$ etc. The minimum detector 24 can conclude a resurgence of tissue impedance, i.e. crossing a minimum, when the impedance value $\underline{Z}_{m+k}$ is at least 5% higher or higher by another specified impedance increase threshold $\Delta\underline{Z}$ than at least one of the preceding tissue impedance values. It can also be specified that the minimum detector 24 captures a minimum $\underline{Z}_{min}$ only then, when the actual value $\underline{Z}_{m+k}$ is higher than at least two or more previous impedance values.

Figure 7:
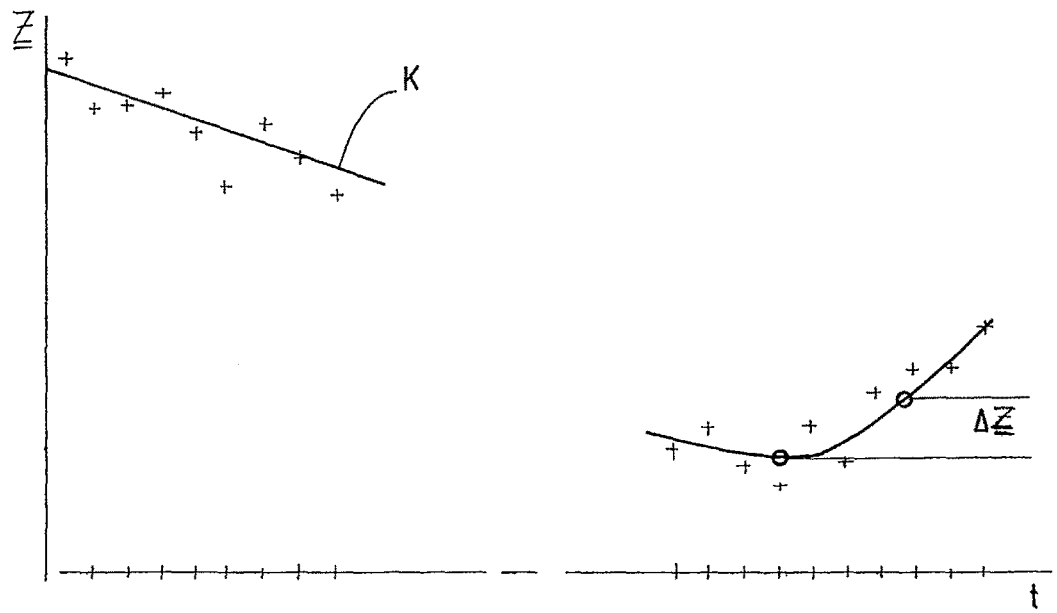

A modification of capturing the minimum by the minimum detector 24 is shown in FIG. 7. There, individual impedance values are shown as crosses that were determined by measuring current and voltage and based on such, the impedance was calculated. These impedance values are subject to arbitrary fluctuations that can result from the microscopic scale of the inhomogeneity that is present in the biological tissue and the denaturing processes that are taking place there. The impedance detector 24 and/or the measuring unit 23 can be configured in such a way that they determine a measured curve K based on individually measured values that approximates the progression of the impedance $\underline{Z}$ over time t. Measured curve K can be determined by splines of the nth degree or according to best-fit algorithms, for example, the method of the smallest error square or other suitable means. As measured curve K, polynomials, straight lines, parables and other sloped curves and combinations of such come into consideration. For example, essentially linear measured value progressions can be approximated by straight lines and nonlinear measured value progressions by parabolic sections. With the help of the progression of measured curve K it can then be determined when the maximum increase in impedance $\Delta\underline{Z}$ has been exceeded. This can be accomplished by detecting that the ascent of curve K is positive. To capture this circumstance it can be detected whether and that a positive increase in impedance $\Delta\underline{Z}$ is present that exceeds a limit value of, for example, 5% of the lowest tissue impedance $\underline{Z}_{min}$.

Figure 8:
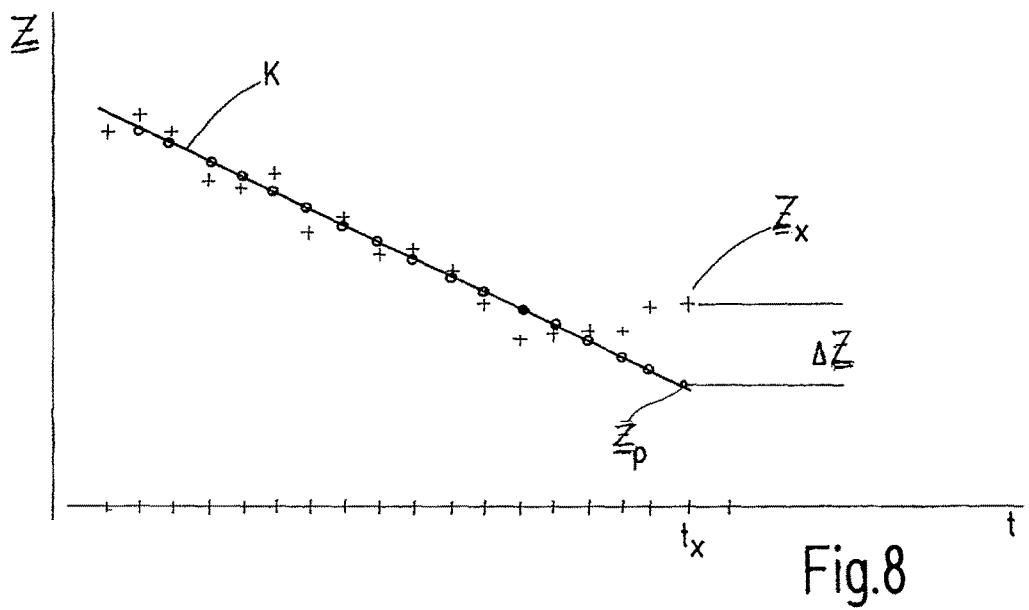

The aforementioned methods capture the impedance minimum after it has been passed due to the resurgence of the impedance that occurs. However, it is also possible to determine reaching the minimum or crossing the minimum at an earlier point in time. That is shown in FIG. 8. The small crosses in the diagram symbolize the tissue impedances determined at each respective point in time t. Measured curve K is a regression line. It contains idealized impedance values that are respectively indicated by a small circle. The minimum detector determines these idealized values, i.e. the impedance values to be expected upon ideal tissue behavior, and compares the respectively last idealized impedance value with the last measured impedance value. In FIG. 8 the tissue impedance $\underline{Z}_x$ has been determined at a point in time $t_x$. Curve K provides the impedance prognosis $\underline{Z}_p$. The difference $\Delta\underline{Z}$ between impedance prognosis $\underline{Z}_p$ and the actual tissue impedance $\underline{Z}_x$ reaches or exceeds a threshold of, for example, once again 5% of the prognosis value $\underline{Z}_p$. The minimum detector can be configured in such a way that it responds by displaying the reaching and crossing of the minimum $\underline{Z}_{min}$ of the tissue impedance $\underline{Z}$. In place of the 5% threshold cited above, other threshold values and criteria can be specified.

The proposed generator 12 determines a resurgence of tissue impedance $\underline{Z}$ indicating the start of desiccation of the tissue 16 and thus also the formation of vapor. By reducing the voltage $U_{App}$ applied, spark formation is avoided. On the other hand, at the start of applying current to the biological tissue 16, elevated voltage (e.g. $U_{App} \geq 2^*U_{Ein}$) is applied, which results in very fast coagulation. The otherwise present disadvantageous effects that appear when excessive voltage is applied such as tearing of tissue, rupturing of vessels, undesired spark formation and thus carbonization, are avoided.

An arrangement 10 according to an embodiment of the invention includes a device 12 for providing high-frequency voltage $U_{App}$ for contact coagulation of biological tissue 16. The device 12 is configured to operate at the start of the contact coagulation with a very high voltage—normally unsuitable for contact coagulation, but used for spark coagulation—of more than 400V, for example. During the operation of the device 12, the tissue impedance $\underline{Z}$ is monitored. This can occur by continuous measurement of voltage $U_{App}$ and the flowing current $I_{App}$. Based on both, measuring unit 23 continually determines the tissue impedance $\underline{Z}$. A minimum detector 24 is provided for the purpose of detecting when a impedance minimum $\underline{Z}_{min}$ passes through and in the event such is detected, it induces generator control 19 to reduce the voltage $U_{App}$ that is delivered by the device 12 to a value that avoids spark formation as well as the desiccation of the tissue.

What is claimed as new and desired to be protected by Letters Patent of the United States is:

1. An arrangement for contact coagulation of biological tissue having an initial impedance before a coagulation process, the arrangement comprising:
   a generator configured to provide high-frequency voltage and deliver high-frequency current;
   a generator control, by means of which the high-frequency voltage provided by the generator can be influenced;
   an instrument having at least one electrode and being supplied with high-frequency current by the generator;
   a measuring unit configured to monitor the tissue impedance; and
   a minimum detector configured to detect a minimum of the tissue impedance, the minimum detector being connected with the generator control in order to induce the generator, upon detecting a minimum of the tissue impedance, to thereupon provide a reduced high-frequency voltage,
   wherein the generator control has a stored adjustment value representing the reduced high-frequency voltage that is to be applied, and the generator control is equipped to induce the generator when the biological tissue still has its initial impedance at the beginning of the coagulation process to provide voltage higher than that represented by the stored adjustment value.

2. The arrangement of claim 1, wherein the voltage that is to be applied at the beginning of the coagulation process is at least twice as high as the stored adjustment value.

3. The arrangement of claim 1, wherein the generator control is equipped to respond to the detection of a first minimum of the tissue impedance by inducing the generator to provide the voltage that is to be applied at a value that is not higher than the stored adjustment value.

4. The arrangement of claim 1, wherein the generator control is equipped to respond to the detection of a second minimum of the tissue impedance by inducing the generator to provide the voltage that is to be applied at a value that is lower than the stored adjustment value.

5. The arrangement of claim 4, wherein the generator control is equipped to respond to the detection of a second minimum of the tissue impedance by inducing the generator to provide the voltage that is to be applied at a value that is 10% lower than the previously supplied voltage.

6. The arrangement of claim 4, wherein the generator control is equipped to terminate the high-frequency application of the generator when the voltage to be applied has reached a value that does not exceed a specified fraction of the stored adjustment value.

7. The arrangement of claim 1, wherein the stored adjustment value can be specified variable by means of a setting tool.

8. The arrangement of claim 1, wherein the actual tissue impedance is captured at chronological intervals that are smaller than 0.2 msec, preferably at most 0.1 msec.

9. The arrangement of claim 8, wherein the measuring unit is equipped to capture the tissue impedance in scanning windows the duration of which is at least as long as one oscillation period of the voltage.

10. The arrangement of claim 9, wherein the measuring unit is equipped to capture at least one parameter of the voltage that is being applied during the measurement interval, at least one parameter of the flowing current and at least one parameter of the phasing between the voltage applied and the flowing current, and based on such, form a ratio relative to the electric flux density of the phasing between the voltage applied and flowing current that identifies the tissue impedance.

11. The arrangement of claim 8, wherein the measuring unit is equipped to form a moving average value consisting of the tissue resistance values captured during several chronological intervals.

12. The arrangement of claim 10, wherein the minimum detector is equipped upon the determination of an increase in the tissue impedance compared with a previously measured tissue impedance to signal reaching and passing a tissue impedance minimum.

13. The arrangement of claim 10, wherein the minimum detector is equipped to signal upon determination of an increase of the tissue impedance or a smoothed average value of the tissue impedance compared with the lowest tissue impedance of a group of previously measured tissue resistance values, when a tissue impedance minimum has been reached and passed through.

14. The arrangement of claim 1, wherein the minimum detector is equipped to determine the trend of the progression of the tissue impedance in order to make a prognosis for the next tissue impedance that is to be measured, whereby reaching and passing a tissue impedance minimum will be signaled when the next measured tissue impedance is above the next tissue impedance that is to be measured by a predetermined value.

* * * * *